(12) United States Patent
Goto et al.

(10) Patent No.: US 9,540,298 B2
(45) Date of Patent: Jan. 10, 2017

(54) PROCESS FOR PRODUCING AROMATIC DIHYDROXY COMPOUND

(71) Applicant: MITSUI CHEMICALS, INC., Tokyo (JP)

(72) Inventors: Yuya Goto, Takaishi (JP); Takashi Nabeta, Takaishi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/764,344

(22) PCT Filed: Sep. 11, 2014

(86) PCT No.: PCT/JP2014/074088
§ 371 (c)(1),
(2) Date: Jul. 29, 2015

(87) PCT Pub. No.: WO2015/041137
PCT Pub. Date: Mar. 26, 2015

(65) Prior Publication Data
US 2016/0176795 A1 Jun. 23, 2016

(30) Foreign Application Priority Data
Sep. 20, 2013 (JP) .................. 2013-195276

(51) Int. Cl.
*C07C 37/60* (2006.01)
*B01J 29/89* (2006.01)

(52) U.S. Cl.
CPC ............... *C07C 37/60* (2013.01); *B01J 29/89* (2013.01)

(58) Field of Classification Search
None
See application file for complete search history.

(56) References Cited

U.S. PATENT DOCUMENTS

| | | |
|---|---|---|
| 3,849,502 A | 11/1974 | Bourdin |
| 4,396,783 A | 8/1983 | Esposito |
| 4,410,501 A | 10/1983 | Taramasso |
| 4,701,428 A | 10/1987 | Bellussi |
| 5,254,746 A | 10/1993 | Costantini et al. |
| 5,426,244 A | 6/1995 | Sugai |
| 2001/0016187 A1* | 8/2001 | Zhou ............... B01J 21/18 423/582 |

FOREIGN PATENT DOCUMENTS

| | | | | |
|---|---|---|---|---|
| IN | 189405 | * | 2/2003 | ............ C07C 39/04 |
| JP | 466546 | | 3/1992 | |
| JP | 5170684 A2 | | 7/1993 | |
| JP | 11165074 A2 | | 6/1999 | |
| JP | 2000219648 A2 | | 8/2000 | |
| JP | 2000239205 A2 | | 9/2000 | |
| JP | 2001158756 A2 | | 6/2001 | |
| JP | 2002105011 A2 | | 4/2002 | |
| JP | 2002187861 | * | 7/2002 | ............ C07C 37/60 |

OTHER PUBLICATIONS

Thangaraj et al. ("Solvent effects in the hydroxylation of phenol with H2O2 over TS-1", Indian Journal of Chemistry, vol. 33A, Mar. 1994, pp. 255-258).*
Wilkenhoner et al. ("Influence of Pore and Crystal Size of Crystalline Titanosilicates on Phenol Hydroxylation in Different Solvents" Journal of Catalysis, 203, 2001, pp. 201-212).*
International Search Report dated Dec. 16, 2014 filed in PCT/JP2014/074088.
Lu, Jiqing. et al., "Effect of composition and promoters in Au/TS-1 catalysts for direct propylene epoxidation using H2 and O2," Catalysis Today 147, 2009, pp. 186-195.
Atoguchi T, et al., "Phenol oxidation over titanosilicalite-1: experimental and DFT study of solvent," J Mol Catal A Chem, Nov. 20, 2001, vol. 176, No. 1/2, pp. 173-178.

* cited by examiner

*Primary Examiner* — Rosalynd Keys
(74) *Attorney, Agent, or Firm* — Rankin, Hill & Clark LLP

(57) ABSTRACT

[Problem] To provide a process for producing an aromatic dihydroxy compound, in which a hydroquinone compound is highly selectively produced while suppressing formation of by-products derived from a solvent and maintaining a high yield based on hydrogen peroxide when a phenol compound is allowed to react with hydrogen peroxide.
[Solution] A process for producing an aromatic dihydroxy compound, including allowing a phenol compound to react with hydrogen peroxide in the presence of a titanosilicate, a C4-C5 alcohol containing a tertiary or quaternary carbon, and water and/or methanol, the amount of the water and/or methanol being 5 to 90 mass % based on the total mass of the reaction liquid.

10 Claims, No Drawings

PROCESS FOR PRODUCING AROMATIC DIHYDROXY COMPOUND

TECHNICAL FIELD

The present invention relates to a process for producing an aromatic dihydroxy compound by allowing a phenol compound to react with hydrogen peroxide using a titanosilicate as a catalyst.

BACKGROUND ART

Aromatic dihydroxy compounds are important as various organic synthesis intermediates or raw materials, and are utilized in fields of reducing agents, rubber chemicals, dyes, medicines, agricultural chemicals, polymerization inhibitors, antioxidants, etc. On that account, improvements are always being required for processes for producing aromatic dihydroxy compounds. Examples of the aromatic dihydroxy compounds obtained by allowing a phenol compound to react with hydrogen peroxide include hydroquinone and catechol, and depending upon the production process, the product ratio between hydroquinone and catechol varies. In recent years, a process particularly for highly selectively producing hydroquinone has been eagerly desired from the viewpoint of a demand and supply balance between hydroquinone and catechol.

As processes for producing aromatic dihydroxy compounds by allowing a phenol compound to react with hydrogen peroxide, a process using an inorganic acid as a catalyst [patent literature 1], a process using a titanosilicate as a catalyst [patent literature 2], etc. are known. In these processes, however, the hydroquinone/catechol product ratio (by mol) is not more than 1.5, and a process for more highly selectively producing hydroquinone is being desired.

As methods for improving selectivity for hydroquinones, a method using a titanosilicate as a catalyst and using a cyclic ether such as dioxane as a solvent [patent literature 3], a method using an aliphatic polyether compound such as ethylene glycol dimethyl ether [patent literature 4] and a method using a polyalkylene glycol monoether compound such as polyethylene glycol mono-4-octyl phenyl ether [patent literature 5] have been developed. In these methods, however, there are problems that by-products derived from a solvent used are formed because the solvent is liable to react with hydrogen peroxide and that the yield based on hydrogen peroxide is lowered because of formation of these by-products.

CITATION LIST

Patent Literature

Patent literature 1: U.S. Pat. No. 3,849,502
Patent literature 2: U.S. Pat. No. 4,396,783
Patent literature 3: JP-A 1993-170684
Patent literature 4: JP-A 2001-158756
Patent literature 5: JP-A 2002-105011

SUMMARY OF INVENTION

Technical Problem

Under such circumstances as previously described, the present invention addresses the problem of providing a process for producing an aromatic dihydroxy compound, in which a hydroquinone compound is highly selectively produced while suppressing formation of by-products derived from a solvent and maintaining a high yield based on hydrogen peroxide when a phenol compound is allowed to react with hydrogen peroxide.

Solution to Problem

The present invention is a process for producing an aromatic dihydroxy compound, comprising allowing a phenol compound to react with hydrogen peroxide in the presence of a titanosilicate, a C4-C5 alcohol containing a tertiary or quaternary carbon, and water and/or methanol, the amount of the water and/or methanol being 5 to 90 mass % based on the total mass of the reaction liquid.

The water and/or methanol is preferably present in an amount of 8 to 90 mass % based on the total mass of the reaction liquid.

In the above process, the amount of the titanosilicate is preferably 0.1 to 30 mass % in terms of an external ratio based on the total mass of the reaction liquid.

The amount of the C4-C5 alcohol containing a tertiary or quaternary carbon used is preferably 1 to 90 mass % based on the total mass of the reaction liquid.

The C4-C5 alcohol containing a tertiary or quaternary carbon is preferably t-butyl alcohol, 2-methyl-1-propanol, 2-methyl-1-butanol, 3-methyl-1-butanol, 2,2-dimethyl-1-propanol, 2-methyl-2-butanol or 3-methyl-2-butanol.

It is preferable that the reaction is carried out on a suspended bed and a catalyst separation step is included. It is preferable that the catalyst having been separated in the catalyst separation step is subjected to a drying treatment and the resulting catalyst is reused for the reaction.

It is preferable that the drying treatment of the catalyst is carried out at 60 to 800° C.

It is preferable that the catalyst separation step comprises continuously drawing out a liquid phase from the reaction liquid containing the catalyst.

It is preferable that the C4-C5 alcohol containing a tertiary or quaternary carbon and the water and/or methanol are separated at the same time by means of distillation from the reaction liquid from which the catalyst has been separated, and a part or all of them are reused for the reaction. Further, it is preferable that the catalyst having been separated in the catalyst separation step or the catalyst having been separated in the catalyst separation step and then subjected to the drying treatment is dispersed in the C4-C5 alcohol containing a tertiary or quaternary carbon and the water and/or methanol having been separated in the distillation step, and the resulting dispersion is fed to a reactor.

Advantageous Effects of Invention

According to the process of the present invention, the solvent is hardly oxidized, and therefore, wasteful consumption of hydrogen peroxide is reduced, a high yield based on hydrogen peroxide is maintained, and production of hydroquinone compound with high selectivity is made possible. On this account, it becomes feasible to produce a hydroquinone compound without being influenced by a demand and supply balance between a hydroquinone compound and a catechol compound, so that the process of the present invention is of industrial significance.

DESCRIPTION OF EMBODIMENTS

The phenol compound used in the present invention includes unsubstituted phenol and substituted phenols.

Examples of the substituted phenol include alkylphenols substituted by a straight-chain or branched alkyl group(s) having 1 to 6 carbon atoms, such as methyl group, ethyl group, isopropyl group, butyl group and hexyl group, or a cycloalkyl group(s).

Examples of the phenol compound include phenol, 2-methylphenol, 3-methylphenol, 2,6-dimethylphenol, 2,3,5-trimethylphenol, 2-ethylphenol, 3-isopropylphenol, 2-butylphenol and 2-cyclohexylphenol. In particular, phenol is preferable. When the phenol compound has substituents at both of the 2-position and the 6-position, the product is a hydroquinone derivative only.

Specific examples of the aromatic dihydroxy compound that is a reaction product include a hydroquinone compound (substituted or unsubstituted hydroquinone) and a catechol compound (substituted or unsubstituted catechol), and include more specifically, hydroquinone, catechol, 2-methylhydroquinone, 3-methylcatechol, 4-methylcatechol, 3-methylhydroquinone, 1,4-dimethylhydroquinone, 1,4-dimethylcatechol, 3,5-dimethylcatechol, 2,3-dimethylhydroquinone, and 2,3-dimethylcatechol The present invention can be carried out by any of a batch process, a semi-batch process and a continuous flow process. For packing a catalyst, various methods such as fixed bed method, fluidized bed method, suspended bed method and tray type fixed bed method can be adopted, and packing of a catalyst may be carried out by any of these methods.

In the present invention, the total mass of the reaction liquid is the total mass of liquid components in the reaction system. That is to say, the total mass does not include a mass of a solid component such as the titanosilicate.

Examples of the liquid components in the reaction system include the phenol compound, hydrogen peroxide, the C4-C5 alcohol containing a tertiary or quaternary carbon, water and/or methanol, the aromatic dihydroxy compound and a reaction by-product. If necessary, other solvents, etc. may be included within limits not detrimental to the effect of the present invention. With progress of the reaction, the amount of the reaction product increases, but the total mass of the reaction liquid during reaction is substantially constant.

The composition of the titanosilicate used as a catalyst in the present invention is that of a structure represented by $(SiO_2)_x \cdot (TiO_2)_{(1-x)}$. The value of $x/(1-x)$ is in the range of 5 to 1000, preferably 10 to 500. The titanosilicate can be prepared by a publicly known process. For example, a process comprising subjecting an alkoxide of silicon and an alkoxide of titanium to a hydrothermal synthesis in the presence of a quaternary ammonium salt or the like is general, as described in U.S. Pat. No. 4,410,501 and Catalysis Today 147 (2009), 186-195. When the quaternary ammonium salt used is a tetrapropyl ammonium salt, the resulting titanosilicate has an MFI structure, and such a titanosilicate is preferably used. As the MFI type titanosilicate, a commercially available one may be used as long as the $(SiO_2)_x \cdot (TiO_2)_{(1-x)}$ is within a given range.

Although the titanosilicate catalyst may be used as it is, it may be used after it is molded according to the packing method for the catalyst. As a method for molding the catalyst, extrusion molding, tablet making, tumbling granulation, spray granulation or the like is generally used. When the catalyst is used in the fixed bed method, extrusion molding or tablet making is preferable. In the case of the suspended bed method, spray granulation is preferable, and as described in, for example, U.S. Pat. No. 4,701,428, a method comprising mixing a titanosilicate suspension prepared in advance with a silica raw material and carrying out spray granulation using a spray dryer is a general method. As the silica raw material, an alkoxide of silicon, a colloidal silica, dissolved silica in water, a sodium silicate (water glass), a potassium silicate or the like can be used. However, if metallic impurities other than silicon are contained, evil influence is exerted on the catalytic performance, and therefore, preferable are the alkoxide of silicon, the colloidal silica and the dissolved silica in water in each of which the amounts of impurities are small. After the spray granulation, drying or calcining may be carried out. The mean particle diameter of the molded catalyst obtained by spray granulation is preferably in the range of 0.1 μm to 1000 μm, more preferably 5 μm to 100 μm. When the mean particle diameter of the molded catalyst is not less than 0.1 μm, handling of the catalyst, such as filtration, can be easily made, so that such a mean particle diameter is preferable. When the mean particle diameter thereof is not more than 1000 μm, the catalyst has good performance and high strength, so that such a mean particle diameter is preferable.

The amount of the titanosilicate catalyst used is preferably in the range of 0.1 to 30 mass %, more preferably 0.4 to 20 mass %, in terms of an external ratio based on the total mass of the reaction liquid. When the amount of the catalyst is not less than 0.1 mass %, the reaction is completed in a short period of time and productivity is enhanced, so that such an amount is preferable. When the amount thereof is not more than 30 mass %, the amount of the catalyst to be separated and recovered is small, so that such an amount is preferable.

The molar ratio of hydrogen peroxide to the phenol compound is preferably not less than 0.01 but not more than 1. Although the concentration of hydrogen peroxide used is not specifically restricted, a usual aqueous solution having a concentration of 30% may be used, or an aqueous hydrogen peroxide solution of a higher concentration may be used as it is or may be used after it is diluted with a solvent that is inert in the reaction system. Examples of the solvent used for dilution include an alcohol compound and water. Hydrogen peroxide may be added at once or may be added little by little over a long period of time.

Examples of the C4-C5 alcohol containing a tertiary or quaternary carbon for use in the present reaction include t-butyl alcohol, 2-methyl-1-propanol, 2-methyl-1-butanol, 3-methyl-1-butanol, 2,2-dimethyl-1-propanol, 2-methyl-2-butanol and 3-methyl-2-butanol. Of these, t-butyl alcohol, 2,2-dimethyl-1-propanol and 2-methyl-2-butanol are preferable. When such an alcohol compound is contained, selectivity for a hydroquinone compound can be enhanced.

It is known that an alcohol such as methanol is coordinated to Ti of a titanosilicate to accelerate oxidation reaction due to hydrogen peroxide. It is presumed that the C4-C5 alcohol containing a tertiary or quaternary carbon, such as t-butyl alcohol, has a moderately bulky structure, and when it is coordinated to Ti, the para position of the phenol compound is selectively oxidized by virtue of steric hindrance around Ti. However, it is presumed that in the case of a more bulky alcohol, improvement in selectivity is not observed because such an alcohol cannot get into a pore of the titanosilicate or is hardly coordinated to Ti.

The amount of the C4-C5 alcohol containing a tertiary or quaternary carbon used is preferably in the range of 1 to 90 mass %, more preferably 3 to 50 mass %, based on the total mass of the reaction liquid.

An amount of not less than 1 mass % is preferable from the viewpoint of high selectivity for the hydroquinone compound, and an amount of not more than 90 mass % is preferable from the viewpoints of a high reaction rate and a small amount of a solvent recovered.

As the water and/or methanol in the present invention, water may be used, or methanol may be used, or water and methanol may be used in combination in an arbitrary ratio.

It is known that when a protic solvent is present, an oxidation active species is stabilized, or proton transfer is accelerated. It is presumed that by the use of water or methanol, protic small molecules thereof stabilize an oxidation active species or accelerate proton transfer also in the present reaction, whereby the reaction is accelerated.

The water may be water contained in the aqueous hydrogen peroxide solution. The amount of the water and/or methanol is preferably in the range of 5 to 90 mass %, more preferably in the range of 8 to 90 mass %, still more preferably in the range of 8 to 85 mass %, based on the total mass of the reaction liquid.

Since the yield of the aromatic dihydroxy compound is high and the selectivity for the hydroquinone compound can be enhanced, the lower limit of the amount of the water and/or methanol is preferably not less than 5 mass %, more preferably not less than 8 mass %, more preferably not less than 9 mass %, more preferably not less than 12 mass %, more preferably not less than 20 mass %, more preferably not less than 30 mass %, more preferably not less than 40 mass %, and more preferably not less than 50 mass %.

When the upper limit thereof is not more than 90 mass %, selectivity for the hydroquinone compound is high, the reaction rate is high, and the amount of the solvent recovered is small.

It is desirable that in the reaction liquid, the reaction raw materials (the phenol compound, hydrogen peroxide) are contained in amounts of 10 to 94 mass %, preferably 13 to 80 mass %. When the amounts of the reaction raw materials are in this range, a desired aromatic dihydroxy compound can be efficiently produced by the process of the present invention.

It is desirable that the ratio (mass ratio) between the amount of the C4-C5 alcohol containing a tertiary or quaternary carbon used and the amount of the water/methanol used (C4-C5 alcohol containing a tertiary or quaternary carbon:water/methanol) is 1:99 to 90:10, preferably 3:97 to 80:20.

When the ratio between them is the above ratio, the yield of the aromatic dihydroxy compound is high, and the selectivity for the hydroquinone compound is enhanced.

The reaction temperature is preferably in the range of 30° C. to 130° C., more preferably 40° C. to 100° C. Also at temperatures other than the temperatures of the above range, the reaction proceeds, but from the viewpoint of enhancement of productivity, the above range is preferable. The reaction pressure is not specifically restricted.

The present reaction may be carried out batchwise, or may be carried out semi-batchwise, or may be carried out continuously. When the reaction is carried out continuously, the reaction may be carried out in a suspension type homogeneous mixing tank or in a fixed bed flow type plug flow reactor model. Further, plural reactors may be connected in series and/or in parallel. The number of reactors is preferably 1 to 4 from the viewpoint of equipment cost. When plural reactors are used, hydrogen peroxide may be divisionally placed in them.

When the present reaction is carried out on a suspended bed, it is preferable that a step of separating the catalyst from the reaction liquid is included. For the separation of the catalyst, precipitation separation, centrifugal filter, pressure filter, filter press, leaf filter, rotary filer or the like is used. In the case of a continuous filter such as rotary filter, a concentrated catalyst suspension, which is the one after a liquid phase is drawn out from the reaction liquid containing the catalyst, can be used for the reaction again. When the reaction is carried out continuously, the liquid phase is continuously drawn out. When the catalyst is taken out as not a suspension but a cake or powder, it may be used for the reaction again as it is, or it may be used for the reaction again after it is subjected to a drying treatment (also referred to as "regeneration treatment"). For the drying treatment, tray dryer, band dryer, rotary dryer, spray dryer, flash dryer or the like is used. The drying treatment can be carried out in an atmosphere of an inert gas such as nitrogen, an atmosphere of air, an atmosphere of air diluted with an inert gas, an atmosphere of water vapor, an atmosphere of water vapor diluted with an inert gas, or the like. The drying temperature is preferably 60 to 800° C., particularly preferably 80 to 600° C. When the drying temperature is this temperature, organic substances having adhered can be reduced without markedly deteriorating performance of the catalyst. The drying treatment can be also carried out by combining plural different temperature regions.

In order to obtain a dihydroxy compound from the reaction liquid, a purification treatment such as removal of unreacted components and by-products may be carried out on the reaction liquid or a separate liquid containing a dihydroxy compound, said separate liquid being the one after separation of the catalyst. The purification treatment can be carried out more preferably on the separate liquid containing a dihydroxy compound, said separate liquid being the one after separation of the catalyst. The method for the purification treatment is not specifically restricted, and specific examples of the methods include oil/water separation, extraction, distillation, crystallization and combinations of these methods. The method, the procedure, etc. of the purification treatment are not specifically restricted, but for example, the following method makes it possible to purify the reaction liquid and the separate liquid containing a dihydroxy compound, said separate liquid being obtained after separation of the catalyst.

When the reaction liquid separates into 2 phases of an oil phase and an aqueous phase, oil/water separation is possible. By the oil/water separation, an aqueous phase having a low content of a dihydroxy compound is removed, and an oil phase is recovered. In this case, from the aqueous phase thus separated, the dihydroxy compound may be recovered by extraction or distillation, or a part or all of the aqueous phase may be used for the reaction again. It is possible to disperse the catalyst having been separated in the catalyst separation step or the catalyst having been subjected to a drying treatment in the separated aqueous phase and to feed the resulting dispersion to the reactor. On the other hand, the oil phase is desirably further subjected to a purification treatment through extraction, distillation, crystallization and the like.

For the extraction, a solvent such as 1-butanol, toluene, isopropyl ether or methyl isobutyl ketone is used. By combining extraction with oil/water separation, it becomes feasible to efficiently carry out the oil/water separation. It is preferable that the extraction solvent is separated and recovered by a distillation column, then recycled.

The distillation may be carried out on the reaction liquid, which is the one just after the catalyst separation, or may be carried out on the oil phase and the aqueous phase, which are the ones after the oil/water separation. Further, the extraction liquid may be distilled.

In the case where the reaction liquid, which is the one just after the catalyst separation, is distilled, it is preferable to separate low-boiling components such as water and an alcohol compound first. Water and the alcohol compound may be separated by different distillation columns, or may be separated by one distillation column. In the present invention, it is desirable to separate water, methanol and the C4-C5 alcohol containing a tertiary or quaternary carbon at the same time by distillation.

A part or all of the thus separated water, methanol and C4-C5 alcohol compound containing a tertiary or quaternary carbon may be used for the reaction again. Further, it is also possible to disperse the catalyst having been separated in the catalyst separation step or the catalyst having been subjected to drying treatment in the thus separated water, methanol or C4-C5 alcohol compound containing a tertiary or quaternary carbon and to feed the resulting dispersion to the reactor.

After water or the alcohol compound is separated by the operation of oil/water separation, extraction, distillation or the like, the phenol compound may be recovered by the next distillation operation and may be used for the reaction again. When water remaining unseparated is contained in the recovered phenol compound, the water can be removed by adding isopropyl ether or toluene and performing azeotropic distillation. This azeotropic distillation can be carried out also on the liquid, which is the one before the recovery of the phenol compound and after the separation of water or the alcohol compound. The thus separated water may be used for the reaction again or may be treated as wastewater. When impurities such as a reaction by-product other than water are contained in the recovered phenol compound, the impurities can be also further separated by a distillation operation. When the impurities are a benzoquinone compound that is a reaction by-product, they can be fed to the reactor again together with the phenol compound.

After the separation of the phenol compound, the hydroquinone compound and the catechol compound can be separated by removing a component having a higher boiling point than the aromatic dihydroxy compound by distillation, and carrying out the next distillation operation. Further, by drawing out the hydroquinone compound from a middle tray of the distillation column, the high-boiling component, the hydroquinone compound and the catechol compound can be separated by one distillation operation.

By removing impurities through distillation or crystallization when needed, purity of the resulting hydroquinone compound and catechol compound can be enhanced.

The thus obtained aromatic dihydroxy compounds such as hydroquinone are useful as various organic synthesis intermediates or raw materials, and are utilized in fields of reducing agents, rubber chemicals, dyes, medicines, agricultural chemicals, polymerization inhibitors, antioxidants, etc.

EXAMPLES

The present invention will be described in more detail with reference to the following examples, but it should be construed that the present invention is in no way limited to those examples.

Yield of aromatic dihydroxy compound (%)=[(number of moles of hydroquinone produced)+(number of moles of catechol produced)]÷(number of moles of hydrogen peroxide added)×100

Hydroquinone/catechol ratio=(number of moles of hydroquinone produced)÷(number of moles of catechol produced)×100

Yield of solvent oxide (%)=(number of moles of solvent oxide produced)÷(number of moles of hydrogen peroxide added)×100

Mass fraction of water or methanol in reaction liquid (%)=[(mass of water or methanol added)+(mass of water contained in hydrogen peroxide solution added)]÷(total mass of reaction liquid)×100

Example 1

In a flask having an internal volume of 50 mL and equipped with a condenser, a thermometer, a feed pump and a magnetic stirrer chip, 0.65 g of a titanosilicate (TS-1) catalyst prepared by the process described in Catalysis Today 147 (2009), 186-195, 6.2 g of phenol, 4 mL of t-butyl alcohol and 6 mL of water were placed, and they were heated to 50° C. in an oil bath while stirring with the stirrer. To the contents in the flask, 0.46 g of a 34% aqueous hydrogen peroxide solution was dropwise added through the feed pump over a period of 10 minutes, and they were held for 190 minutes as they were. After the reaction liquid was cooled, the catalyst was filtered off, and a part of the reaction liquid was withdrawn. The residual hydrogen peroxide was determined by iodometry, and the product was determined by gas chromatography.

As a result, the yield of aromatic dihydroxy compounds was 57%, the hydroquinone/catechol ratio was 4.1, and the yield of a solvent oxide was not more than 1%.

[Analytical Conditions of Gas Chromatography]
Detector: flame ionization detector (FID)
Column: DB-5 (Agilent J&W), inner diameter 0.25 mm, length 60 m, film thickness 0.25 μm
Column temperature: maintained at 80° C. for 10 minutes and elevated up to 280° C. at a temperature elevation rate of 4° C./min
Injection port temperature: 280° C.
Detector temperature: 280° C.
Carrier gas: helium
Flow rate: 80 mL/min Example 2

Operations were carried out in the same manner as in Example 1, except that 3.2 g of 2,2-dimethyl-1-propanol was used instead of t-butyl alcohol. As a result, the yield of aromatic dihydroxy compounds was 37%, the hydroquinone/catechol ratio was 4.8, and the yield of a solvent oxide was not more than 1%.

Example 3

Operations were carried out in the same manner as in Example 1, except that 4 mL of 2-methyl-2-butanol was used instead of t-butyl alcohol. As a result, the yield of aromatic dihydroxy compounds was 48%, the hydroquinone/catechol ratio was 4.5, and the yield of a solvent oxide was not more than 1%.

Comparative Example 1

Operations were carried out in the same manner as in Example 1, except that 4 mL of 1,4-dioxane was used instead of t-butyl alcohol. As a result, the yield of aromatic dihydroxy compounds was 38%, the hydroquinone/catechol ratio was 5.1, and the yield of a solvent oxide was 24%.

Comparative Example 2

Operations were carried out in the same manner as in Example 1, except that 10 mL of water was used instead of 4 mL of t-butyl alcohol and 6 mL of water. As a result, the yield of aromatic dihydroxy compounds was 63%, and the hydroquinone/catechol ratio was 0.9.

Comparative Example 3

Operations were carried out in the same manner as in Example 1, except that 4 mL of methanol was used instead of t-butyl alcohol. As a result, the yield of aromatic dihydroxy compounds was 49%, and the hydroquinone/catechol ratio was 1.2.

Comparative Example 4

Operations were carried out in the same manner as in Example 1, except that 4 mL of 1-butanol was used instead of t-butyl alcohol. As a result, the yield of aromatic dihydroxy compounds was 17%, and the hydroquinone/catechol ratio was 0.7.

Comparative Example 5

Operations were carried out in the same manner as in Example 1, except that 4 mL of 1-hexanol was used instead of t-butyl alcohol. As a result, the yield of aromatic dihydroxy compounds was 1.6%, and the hydroquinone/catechol ratio was 0.

Comparative Example 6

Operations were carried out in the same manner as in Example 1, except that 4 mL of 2-propanol was used instead of t-butyl alcohol. As a result, the yield of aromatic dihydroxy compounds was 24%, and the hydroquinone/catechol ratio was 1.2.

Comparative Example 7

Operations were carried out in the same manner as in Example 1, except that 4 mL of 2-butanol was used instead of t-butyl alcohol. As a result, the yield of aromatic dihydroxy compounds was 18%, and the hydroquinone/catechol ratio was 1.5.

Comparative Example 8

Operations were carried out in the same manner as in Example 1, except that 4 mL of 3-methyl-3-pentanol was used instead of t-butyl alcohol. As a result, the yield of aromatic dihydroxy compounds was 13%, and the hydroquinone/catechol ratio was 1.7.

Comparative Example 9

Operations were carried out in the same manner as in Example 1, except that 4 mL of 3-ethyl-3-pentanol was used instead of t-butyl alcohol. As a result, the yield of aromatic dihydroxy compounds was 61%, and the hydroquinone/catechol ratio was 1.3.

Comparative Example 10

Operations were carried out in the same manner as in Example 1, except that 4 mL of cyclohexanol was used instead of t-butyl alcohol. As a result, the yield of aromatic dihydroxy compounds was 15%, and the hydroquinone/catechol ratio was 1.5.

Comparative Example 11

Operations were carried out in the same manner as in Example 1, except that 3.7 g of 1-methylcyclchexanol was used instead of t-butyl alcohol. As a result, the yield of aromatic dihydroxy compounds was 32%, and the hydroquinone/catechol ratio was 2.0.

Comparative Example 12

Operations were carried out in the same manner as in Example 1, except that 4 mL of cyclohexanemethanol was used instead of t-butyl alcohol. As a result, the yield of aromatic dihydroxy compounds was 5.9%, and the hydroquinone/catechol ratio was 0.5.

Comparative Example 13

Operations were carried out in the same manner as in Example 1, except that 4 mL of pivalonitrile was used instead of t-butyl alcohol. As a result, the yield of aromatic dihydroxy compounds was 2.8%, and the hydroquinone/catechol ratio was 0.

Comparative Example 14

Operations were carried out in the same manner as in Example 1, except that 4 mL of cyclohexane was used instead of t-butyl alcohol. As a result, the yield of aromatic dihydroxy compounds was 44%, and the hydroquinone/catechol ratio was 0.6.

Comparative Example 15

Operations were carried out in the same manner as in Example 1, except that 4 mL of benzene was used instead of t-butyl alcohol. As a result, the yield of aromatic dihydroxy compounds was 63%, and the hydroquinone/catechol ratio was 0.8.

TABLE 1

| | Solvent | Mass fraction of water or methanol (mass %) | Yield of aromatic dihydroxy compounds (%) | Hydroquinone/catechol ratio | Yield of solvent oxide (%) |
|---|---|---|---|---|---|
| Ex. 1 | t-butyl alcohol, water | 40 | 57 | 4.1 | not more than 1 |
| 2 | 2,2-dimethyl-1-propanol, water | 40 | 37 | 4.8 | not more than 1 |
| 3 | 2-methyl-2-butanol, water | 40 | 48 | 4.5 | not more than 1 |
| Comp. Ex. 1 | dioxane, water | 38 | 38 | 5.1 | 24 |
| 2 | water | 62 | 63 | 0.9 | not more than 1 |

TABLE 1-continued

| | Solvent | Mass fraction of water or methanol (mass %) | Yield of aromatic dihydroxy compounds (%) | Hydro-quinone/catechol ratio | Yield of solvent oxide (%) |
|---|---|---|---|---|---|
| 3 | methanol, water | 60 | 49 | 1.2 | not more than 1 |
| 4 | 1-butanol, water | 40 | 17 | 0.7 | — |
| 5 | 1-hexanol, water | 40 | 1.6 | 0 | — |
| 6 | 2-propanol, water | 40 | 24 | 1.2 | — |
| 7 | 2-butanol, water | 40 | 18 | 1.5 | — |
| 8 | 3-methyl-3-pentanol, water | 39 | 13 | 1.7 | — |
| 9 | 3-ethyl-3-pentanol, water | 39 | 61 | 1.3 | — |
| 10 | cyclohexanol, water | 38 | 15 | 1.5 | — |
| 11 | 1-methylcyclohexanol, water | 39 | 32 | 2.0 | — |
| 12 | cyclohexanemethanol, water | 39 | 5.9 | 0.5 | — |
| 13 | pivalonitrile, water | 40 | 2.8 | 0 | — |
| 14 | cyclohexane, water | 40 | 44 | 0.6 | — |
| 15 | benzene, water | 39 | 63 | 0.8 | — |

Example 4

Operations were carried out in the same manner as in Example 1, except that 6 mL of methanol was used instead of water. As a result, the yield of aromatic dihydroxy compounds was 37%, and the hydroquinone/catechol ratio was 3.5.

Comparative Example 16

Operations were carried out in the same manner as in Example 1, except that 6 mL of ethanol was used instead of water. As a result, the yield of aromatic dihydroxy compounds was 5.5%, and the hydroquinone/catechol ratio was 3.1.

Comparative Example 17

Operations were carried out in the same manner as in Example 1, except that 6 mL of acetonitrile was used instead of water. As a result, the yield of aromatic dihydroxy compounds was 11%, and the hydroquinone/catechol ratio was 0.5.

After the reaction liquid was cooled, the catalyst was filtered off, and a part of the reaction liquid was withdrawn. The residual hydrogen peroxide was determined by iodometry, and the product was determined by GC.

As a result, the yield of aromatic dihydroxy compounds was 41%, and the hydroquinone/catechol ratio was 1.9.

Example 5A

Operations were carried out in the same manner as in Example 5, except that the amount of water was changed to 0.39 mL. As a result, the yield of aromatic dihydroxy compounds was 43%, and the hydroquinone/catechol ratio was 1.6.

Example 6

Operations were carried out in the same manner as in Example 5, except that the amount of water was changed to 1 mL. As a result, the yield of aromatic dihydroxy compounds was 43%, and the hydroquinone/catechol ratio was 2.5.

TABLE 2

| | Solvent | Mass fraction of water or methanol (mass %) | | Yield of aromatic dihydroxy compounds (%) | Hydro-quinone/catechol ratio |
|---|---|---|---|---|---|
| Ex. 1 | t-butyl alcohol, water | 40 | | 57 | 4.1 |
| 4 | t-butyl alcohol, methanol | 35 | | 37 | 3.5 |
| Comp. Ex. 16 | t-butyl alcohol, ethanol | 2 | mass fraction of ethanol 32 mass % | 5.5 | 3.1 |
| 17 | t-butyl alcohol, acetonitrile | 2 | mass fraction of acetonitrile 31 mass % | 11 | 0.5 |

Example 5

In a flask having an internal volume of 50 mL and equipped with a condenser, a thermometer and a magnetic stirrer chip, 0.2 g of a titanosilicate (TS-1) catalyst prepared by the process described in Catalysis Today 147 (2009), 186-195, 6.2 g of phenol, 2 mL of t-butyl alcohol and 0.5 mL of water were placed, and they were heated to 70° C. in an oil bath while stirring with the stirrer. To the contents in the flask, 0.45 g of a 34% hydrogen peroxide solution was added, and they were held for 200 minutes as they were.

Example 7

Operations were carried out in the same manner as in Example 5, except that the amount of water was changed to 3 mL. As a result, the yield of aromatic dihydroxy compounds was 53%, and the hydroquinone/catechol ratio was 3.1.

Example 8

Operations were carried out in the same manner as in Example 5, except that the amount of water was changed to 10 mL. As a result, the yield of aromatic dihydroxy compounds was 56%, and the hydroquinone/catechol ratio was 3.3.

Example 9

Operations were carried out in the same manner as in Example 5, except that the amount of water was changed to 40 mL. As a result, the yield of aromatic dihydroxy compounds was 52%, and the hydroquinone/catechol ratio was 3.4.

Comparative Example 18

Operations were carried out in the same manner as in Example 5, except that water was not used. As a result, the yield of aromatic dihydroxy compounds was 39%, and the hydroquinone/catechol ratio was 1.4.

TABLE 3

|  | Mass fraction of water in reaction liquid (mass %) | Yield of aromatic dihydroxy compounds (%) | Hydroquinone/catechol ratio |
|---|---|---|---|
| Comp. Ex. 18 | 3.6 | 39 | 1.4 |
| Ex. 5A | 8.0 | 43 | 1.6 |
| Ex. 5 | 9.2 | 41 | 1.9 |
| 6 | 14 | 43 | 2.5 |
| 7 | 29 | 53 | 3.1 |
| 8 | 57 | 56 | 3.3 |
| 9 | 84 | 52 | 3.4 |

Example 10

In a separable flask with a hot-water jacket, the separable flask having an internal volume of 500 mL and equipped with a condenser, a thermometer, a catalyst slurry feed line, a phenol/solvent feed line, a hydrogen peroxide solution feed line and a stirring blade, 2.65 g of a titanosilicate (TS-1) catalyst prepared by the process described in Catalysis Today 147 (2009), 186-195, 55.66 g of phenol, 39.75 g of t-butyl alcohol and 82.16 g of water were placed, and they were heated by the hot-water jacket while stirring with the stirring blade until the internal temperature of the reaction liquid became 70° C. This separable flask has a side pipe at the height corresponding to the internal volume of 230 mL, and when the amount of the reaction liquid becomes 230 mL or more, the reaction liquid is removed out of the separable flask by overflow. To the flask, continuous feeding of a titanosilicate (TS-1) catalyst slurry of 4.0 mass % at a rate of 2.98 g/min, a hydrogen peroxide solution of 7.8 mass % at a rate of 0.71 g/min and a mixed solution of phenol and t-butyl alcohol having a phenol concentration of 58.3 mass % at a rate of 3.98 g/min was started, to initiate continuous oxidation reaction under the conditions of a residence time of 30 minutes. 90 minutes after overflow of the reaction liquid was confirmed, the overflow liquid was withdrawn and cooled. Thereafter, the catalyst was filtered off, and a part of the reaction liquid was withdrawn. The residual hydrogen peroxide was determined by iodometry, and the product was determined by gas chromatography.

As a result, the yield of aromatic dihydroxy compounds was 70.1%, the hydroquinone/catechol ratio was 4.8, and the yield of a solvent oxide was not more than 1%.

Example 11

In a flask having an internal volume of 300 mL and equipped with a condenser, a thermometer, a stirring blade and a mechanical stirrer, 10 g of a titanosilicate (TS-1) catalyst prepared by the process described in Catalysis Today 147 (2009), 186-195, 52.5 g of phenol, 50 mL of t-butyl alcohol and 75 mL of water were placed, and they were heated to 70° C. in an oil bath while stirring with the stirrer. To the contents in the flask, 27.9 g of a 34% hydrogen peroxide solution was dropwise added through a feed pump over a period of 120 minutes, and they were held for 60 minutes as they were. After the reaction liquid was cooled, the catalyst was filtered off, and a part of the reaction liquid was withdrawn. The residual hydrogen peroxide was determined by iodometry, and the product was determined by GC.

As a result, the yield of aromatic dihydroxy compounds was 59%, and the hydroquinone/catechol ratio was 4.9.

Example 12

In a flask having an internal volume of 50 mL and equipped with a condenser, a thermometer and a magnetic stirrer chip, the catalyst having been filtered off in Example 11 was placed so that the content of the titanosilicate (TS-1) catalyst might become 0.8 g, then 4.2 g of phenol, 4 mL of t-butyl alcohol and 6 mL of water were placed, and they were heated to 70° C. in an oil bath while stirring with the stirrer. To the contents in the flask, 2.2 g of a 34% hydrogen peroxide solution was dropwise added through a feed pump over a period of 120 minutes, and they were held for 60 minutes as they were. After the reaction liquid was cooled, the catalyst was filtered off, and a part of the reaction liquid was withdrawn. The residual hydrogen peroxide was determined by iodometry, and the product was determined by GC.

As a result, the yield of aromatic dihydroxy compounds was 12%, and the hydroquinone/catechol ratio was 2.0.

Example 13

Operations were carried out in the same manner as in Example 12, except that the catalyst having been filtered off in Example 11 was dried in an air atmosphere at 200° C. for 5 hours. As a result, the yield of aromatic dihydroxy compounds was 46%, and the hydroquinone/catechol ratio was 3.6.

Example 14

Operations were carried out in the same manner as in Example 12, except that the catalyst having been filtered off in Example 11 was dried in an air atmosphere at 400° C. for 5 hours. As a result, the yield of aromatic dihydroxy compounds was 64%, and the hydroquinone/catechol ratio was 4.8.

Example 15

Operations were carried out in the same manner as in Example 12, except that the catalyst having been filtered off in Example 11 was dried in an air atmosphere at 500° C. for 5 hours. As a result, the yield of aromatic dihydroxy compounds was 57%, and the hydroquinone/catechol ratio was 4.2.

TABLE 4

|  | Drying temperature (° C.) | Yield of aromatic dihydroxy compounds (%) | Hydroquinone/ catechol ratio |
|---|---|---|---|
| Ex. 11 | — | 59 | 4.9 |
| Ex. 12 | no drying | 12 | 2.0 |
| Ex. 13 | 200 | 46 | 3.6 |
| Ex. 14 | 400 | 64 | 4.8 |
| Ex. 15 | 500 | 57 | 4.2 |

The invention claimed is:

1. A process for producing an aromatic dihydroxy compound, comprising allowing a phenol compound to react with hydrogen peroxide in the presence of a titanosilicate, a C4-C5 alcohol containing a tertiary or quaternary carbon, and water and/or methanol,
wherein the water and/or methanol is present in an amount of 8 to 90 mass % based on the total mass of the reaction liquid.

2. The process for producing an aromatic dihydroxy compound as claimed in claim 1, wherein the amount of the titanosilicate is 0.1 to 30 mass % in terms of an external ratio based on the total mass of the reaction liquid.

3. The process for producing an aromatic dihydroxy compound as claimed in claim 1, wherein the amount of the C4-C5 alcohol containing a tertiary or quaternary carbon used is 1 to 90 mass % based on the total mass of the reaction liquid.

4. The process for producing an aromatic dihydroxy compound as claimed in claim 1, wherein the C4-C5 alcohol containing a tertiary or quaternary carbon is t-butyl alcohol, 2-methyl-1-propanol, 2-methyl-1-butanol, 3-methyl-1-butanol, 2,2-dimethyl-1-propanol, 2-methyl-2-butanol or 3-methyl-2-butanol.

5. The process for producing an aromatic dihydroxy compound as claimed in claim 1, wherein the reaction is carried out on a suspended bed, the process comprising a catalyst separation step.

6. The process for producing an aromatic dihydroxy compound as claimed in claim 5, comprising subjecting the catalyst having been separated in the catalyst separation step to a drying treatment and reusing the resulting catalyst for the reaction.

7. The process for producing an aromatic dihydroxy compound as claimed in claim 6, wherein the drying treatment of the catalyst is carried out at 60 to 800° C.

8. The process for producing an aromatic dihydroxy compound as claimed in claim 5, wherein the catalyst separation step comprises continuously drawing out a liquid phase from the reaction liquid containing the catalyst.

9. The process for producing an aromatic dihydroxy compound as claimed in claim 5, comprising separating the C4-C5 alcohol containing a tertiary or quaternary carbon and the water and/or methanol at the same time by means of distillation from the reaction liquid from which the catalyst has been separated, and reusing a part or all of them for the reaction.

10. The process for producing an aromatic dihydroxy compound as claimed in claim 9, wherein the catalyst having been separated in the catalyst separation step or the catalyst having been separated in the catalyst separation step and then subjected to the drying treatment is dispersed in the C4-C5 alcohol containing a tertiary or quaternary carbon and the water and/or methanol having been separated by means of the distillation, and the resulting dispersion is fed to a reactor.

* * * * *